(12) United States Patent
Lewis et al.

(10) Patent No.: US 8,795,225 B2
(45) Date of Patent: Aug. 5, 2014

(54) FLUID DETECTION IN AN ENTERAL FEEDING SET

(75) Inventors: Thomas G. Lewis, O'Fallon, IL (US); William J. Byrd, Arnold, MO (US); Joseph A. Hudson, O'Fallon, MO (US)

(73) Assignee: Covidien LP, Mansfield, MA (US)

( * ) Notice: Subject to any disclaimer, the term of this patent is extended or adjusted under 35 U.S.C. 154(b) by 1246 days.

(21) Appl. No.: 12/240,654

(22) Filed: Sep. 29, 2008

(65) Prior Publication Data

US 2010/0082011 A1    Apr. 1, 2010

(51) Int. Cl.
*A61M 5/168* (2006.01)
*A61M 5/142* (2006.01)
*A61J 15/00* (2006.01)
*G01N 21/59* (2006.01)

(52) U.S. Cl.
CPC ....... *A61M 5/16886* (2013.01); *A61M 5/14232* (2013.01); *A61M 2205/331* (2013.01); *A61M 2205/3313* (2013.01); *A61J 2015/0088* (2013.01); *G01N 21/59* (2013.01)
USPC ............... 604/67; 604/65; 604/122; 604/251; 604/253; 604/503

(58) Field of Classification Search
CPC ..................... A61M 5/14232; A61M 5/16886; A61M 5/365; A61M 2205/3306; A61M 2205/331; A61M 2205/3313; A61M 2205/3334; A61M 2205/6081; A61J 2015/008; A61J 2015/0084; A61J 2015/0088; G01N 21/35; G01N 21/59; G01N 21/3577
USPC ........ 604/65–67, 503, 122, 253; 356/28, 422, 356/436; 250/343
See application file for complete search history.

(56) References Cited

U.S. PATENT DOCUMENTS

| | | | |
|---|---|---|---|
| 3,713,743 A | * | 1/1973 | Simms .......................... 356/338 |
| 3,851,976 A | | 12/1974 | Meier |
| 3,993,047 A | * | 11/1976 | Peek .............................. 600/479 |
| 4,005,603 A | | 2/1977 | Golahny et al. |
| 4,075,481 A | | 2/1978 | Stoft et al. |
| 4,300,048 A | | 11/1981 | Barbier et al. |
| 4,312,341 A | | 1/1982 | Zissimopoulos et al. |
| 4,474,206 A | | 10/1984 | Cannon |
| 4,525,069 A | | 6/1985 | Tanaka et al. |
| 4,534,046 A | | 8/1985 | Mihara |
| 4,665,391 A | | 5/1987 | Spani |
| 4,756,274 A | | 7/1988 | Rubino |
| 4,834,497 A | | 5/1989 | Angel |
| 4,865,581 A | * | 9/1989 | Lundquist et al. .............. 600/18 |
| 4,909,797 A | | 3/1990 | Timothy |
| 4,919,649 A | | 4/1990 | Timothy et al. |
| 5,250,027 A | | 10/1993 | Lewis et al. |
| 5,256,155 A | | 10/1993 | Yerlikaya et al. |
| 5,346,466 A | | 9/1994 | Yerlikaya et al. |

(Continued)

*Primary Examiner* — Quynh-Nhu H Vu
*Assistant Examiner* — Larry R Wilson

(57) ABSTRACT

Detection of fluid conditions in an administration set. A light source is positioned to transmit an infrared light through administration set tubing and any fluid therein. A light sensor senses the infrared light transmitted through the tubing and generates an output signal. A frequency of the output signal is a function of an intensity of the light transmitted through the tubing. A processor receives and determines the frequency of the output signal, and compares the determined frequency to threshold frequency values to determine whether fluid is in the tubing. The processor also monitors the generated output signal to determine if the frequency of the output signal changes over time, and determines whether fluid is flowing in the tubing as a function of the determined change in frequency.

25 Claims, 7 Drawing Sheets

(56) References Cited

U.S. PATENT DOCUMENTS

| | | |
|---|---|---|
| 5,357,113 A | 10/1994 | Liston et al. |
| 5,407,638 A | 4/1995 | Wang |
| 5,408,326 A | 4/1995 | Wang |
| 5,415,641 A | 5/1995 | Yerlikaya et al. |
| 5,508,521 A | 4/1996 | Kraft et al. |
| 5,536,935 A | 7/1996 | Klotzsch et al. |
| 5,560,355 A | 10/1996 | Merchant et al. |
| 5,562,615 A | 10/1996 | Nassif |
| 5,575,284 A | 11/1996 | Athan et al. |
| 5,586,567 A | 12/1996 | Smith et al. |
| 5,721,430 A | 2/1998 | Wong |
| 5,767,976 A | 6/1998 | Ankerhold et al. |
| 5,798,699 A | 8/1998 | Bryant et al. |
| 5,828,458 A * | 10/1998 | Taylor et al. ............ 356/440 |
| 5,903,006 A | 5/1999 | Kiuchi et al. |
| 5,920,018 A | 7/1999 | Wilkerson et al. |
| 5,961,450 A | 10/1999 | Merchant et al. |
| 6,011,985 A | 1/2000 | Athan et al. |
| 6,162,183 A | 12/2000 | Hoover |
| 6,219,138 B1 | 4/2001 | Swanson et al. |
| 6,263,227 B1 | 7/2001 | Boggett et al. |
| 6,330,468 B1 | 12/2001 | Scharf |
| 6,370,408 B1 | 4/2002 | Merchant et al. |
| 6,496,711 B1 | 12/2002 | Athan et al. |
| 6,683,679 B2 | 1/2004 | Belenkii |
| 6,949,758 B2 | 9/2005 | Shi et al. |
| 7,032,461 B2 | 4/2006 | Ueki et al. |
| 2002/0036276 A1 | 3/2002 | Seeman |
| 2004/0121494 A1 | 6/2004 | Arno |
| 2005/0267418 A1* | 12/2005 | Fournie et al. ............ 604/249 |
| 2009/0262351 A1* | 10/2009 | Erickson et al. ............ 356/409 |

\* cited by examiner

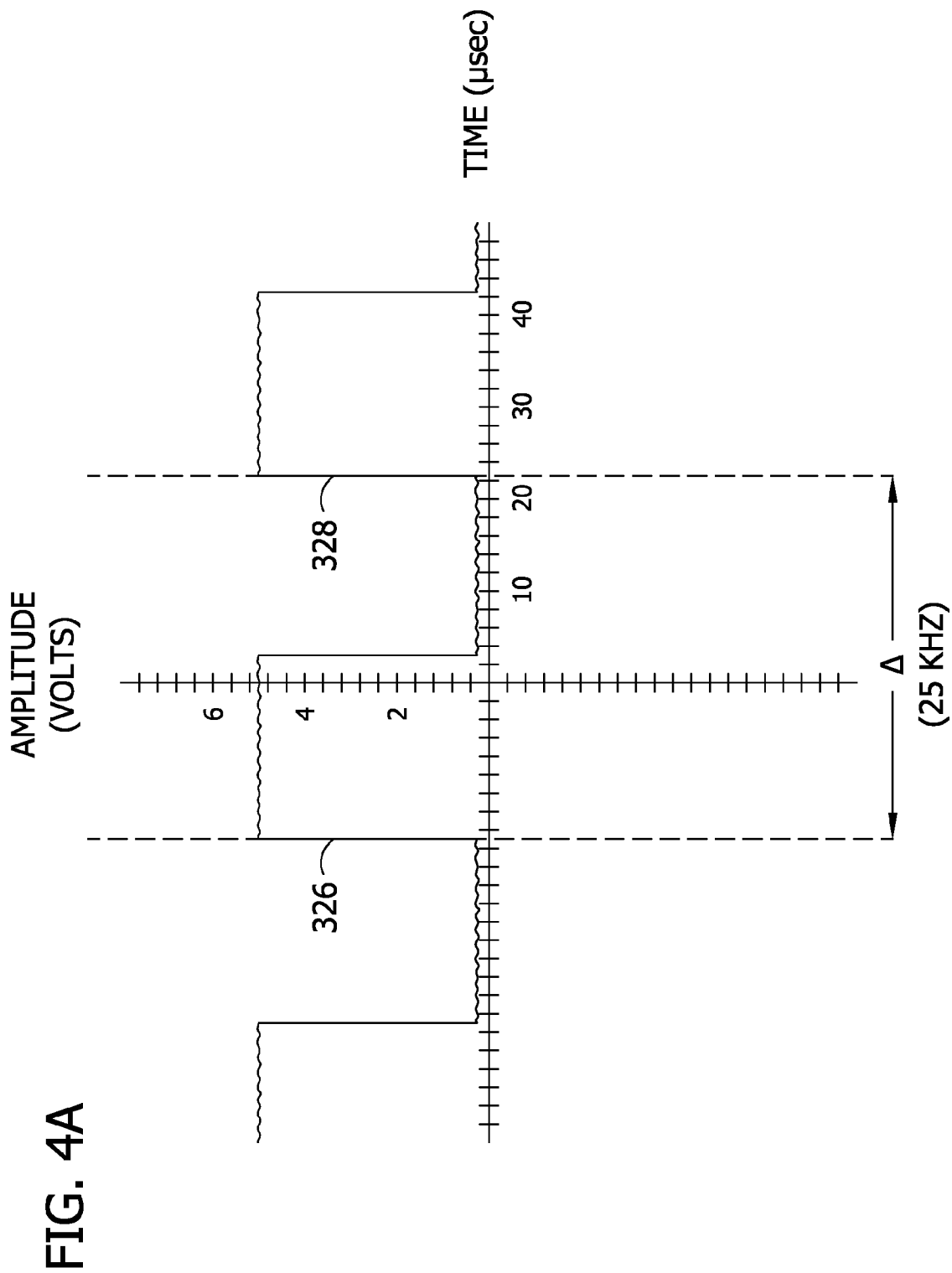

FLUID DETECTION IN AN ENTERAL FEEDING SET

TECHNICAL FIELD

This invention relates generally to the field of fluid administration to patients via administration feeding sets. In particular, the invention relates to a fluid detection system for detecting fluids and/or fluid flow in administration feeding sets.

BACKGROUND

Hospitals and other healthcare facilities often administer food and/or medications to patients via an administration set such as a feeding tube when those patients are unable to take food and/or medications by mouth due to, for example, an inability to swallow. Typically, fluid is delivered to the patient by a pump set loaded on a flow control apparatus, such as a peristaltic pump, which delivers fluid to the patient at a controlled rate of delivery. A peristaltic pump usually comprises a housing that includes a rotor or the like operatively engaged to at least one motor through a gearbox. The rotor drives fluid through tubing routed through the pump set by the peristaltic action effected by rotation of the rotor by the motor. The motor is operatively connected to a rotatable shaft that drives the rotor, which in turn progressively compresses the tubing and drives the fluid at a controlled rate through the pump set. The pump set may have a type of valve mechanism for permitting or preventing fluid flow communication through the pump set. A controller operates the motor or motors used to drive the rotor and, if necessary, controls fluid flow by operation of the valve mechanism.

It is important to monitor the administration of such enteral nutritional fluids being supplied to a patient via a feeding tube to ensure that the patient receives a correct dose of medication and/or a sufficient amount of nutritional fluids. For example, it is important to have the ability to detect whether or not air is the feeding tube, which can be indication whether or not nutritional fluids or medications are being delivered to the patient.

Conventional administration sets often include a drip chamber that is connected between the pump and the patient. As known to those skilled in the art, the drip chamber includes a container typically made from a clear resilient plastic material that allows pinching or squeezing of the container. The drip chamber has associated tubing, which connects the drip chamber into fluid communication with a medical device (e.g., bag or pump) or some other form of apparatus used to control the infusion to a patient and into fluid communication with to a section of tubing delivering fluid to the patient. In an operable state, the drip chamber is partially filled with fluid to establish a fluid level that is somewhere near the midpoint of the container.

Such conventional administration sets often include a fluid level detector associated with the drip chamber for the purpose of monitoring the level of fluid in the drip chamber and, thus, the fluid being delivered to the patient. Unfortunately, the circuitry of such detectors can be quite complex. For example, such fluid level detectors often require circuitry for generating and sensing multiple light paths with respect to a particular expected fluid level in the drip chamber. Moreover, because there are multiple sensing components, such detectors often require the execution of complex algorithms to calculate the fluid level in the drip chamber. Moreover, the drip chamber introduces another component into the administration set, which in addition to adding expense and being altitude dependent, has the potential to fail and, thus, interrupt the delivery of fluid to a patient.

Light to voltage (LTV) converters have been used as fluid detectors for the purpose of monitoring the presence of fluid in the drip chamber. In operation, a light source positioned on one side of the drip chamber transmits a beam of light through the drip chamber and onto a LTV converter positioned on an opposite side of the drip chamber. The LTV converter is responsive to the intensity of the transmitted light to generate a high or low voltage output signal. For example, when the transmitted light is substantially uninterrupted, the LTV converter generates a high voltage output signal. Alternatively, when the transmitted light is interrupted, the LTV converter generates a low voltage output signal. Accordingly, when fluid drips thru the light beam passing through the drip chamber, the light beam is interrupted and a low voltage output signal is generated. However, when the drip chamber is not present, for reasons such as described above, the LTV converter cannot be used to detect fluid flow directly in the feeding tube because of a lack of detectable transitions (e.g., drips) within the feeding tube. That is, in contrast to the drip chamber, there are no reoccurring air-to-fluid transitions when fluid is flowing in the feeding tube. Moreover, LTV converters are not effective in detecting clear fluids.

SUMMARY OF THE INVENTION

Embodiments of the invention overcome one or more deficiencies in known systems by providing a fluid detection system that allows for the elimination of a drip chamber from fluid administration sets while providing accurate information concerning the presence or absence of fluid in the feeding tube.

According to one aspect of the invention, a system is provided for detecting fluid in a feeding tube. A light source transmits an infrared light through the feeding tube and any fluid therein. An infrared sensor senses the infrared light transmitted through the feeding tube and through any fluid therein and generates an output signal having a frequency that is a function of an intensity of the sensed infrared light. A processor receives the generated output signal and determines the frequency of the generated output signal and determines whether fluid is in the feeding tube as a function of the determined frequency.

In another aspect, a system is provided for detecting fluid flow in a feeding tube. The fluid flow is controlled by a pump having a motor for pumping the fluid through the feeding tube. A light source positioned adjacent the feeding tube for transmits an infrared light through the feeding tube and any fluid therein. An infrared sensor positioned adjacent to the feeding tube receives the transmitted infrared light and generates an output signal having a frequency that is a function of an intensity of the sensed infrared light transmitted through the feeding tube. A processor receives the generated output signal and determines whether the frequency of the generated output signal changes over a predetermined period of time. The processor determines whether fluid is flowing in the feeding tube as a function of the determined change in frequency.

A method embodying aspects of the invention is provided for detecting fluid in a feeding tube. The method includes transmitting an infrared light through the feeding tube and any fluid therein. The method also includes sensing the infrared light transmitted through the feeding tube and through any fluid therein and generating an output signal having a frequency that is a function of an intensity of the sensed infrared light transmitted through the feeding tube. The method further includes determining the frequency of the generated output signal and determining whether fluid is in the feeding tube by comparing the determined frequency of the generated output signal to one or more threshold frequency ranges stored in a memory.

Other objects and features of the present invention will be in part apparent and in part pointed out hereinafter.

BRIEF DESCRIPTION OF THE DRAWINGS

FIGS. 4A and 4B are exemplary output signals illustrating light to frequency conversions for fluid detection.

Corresponding reference characters indicate corresponding parts throughout the drawings.

DETAILED DESCRIPTION

Figure 1:
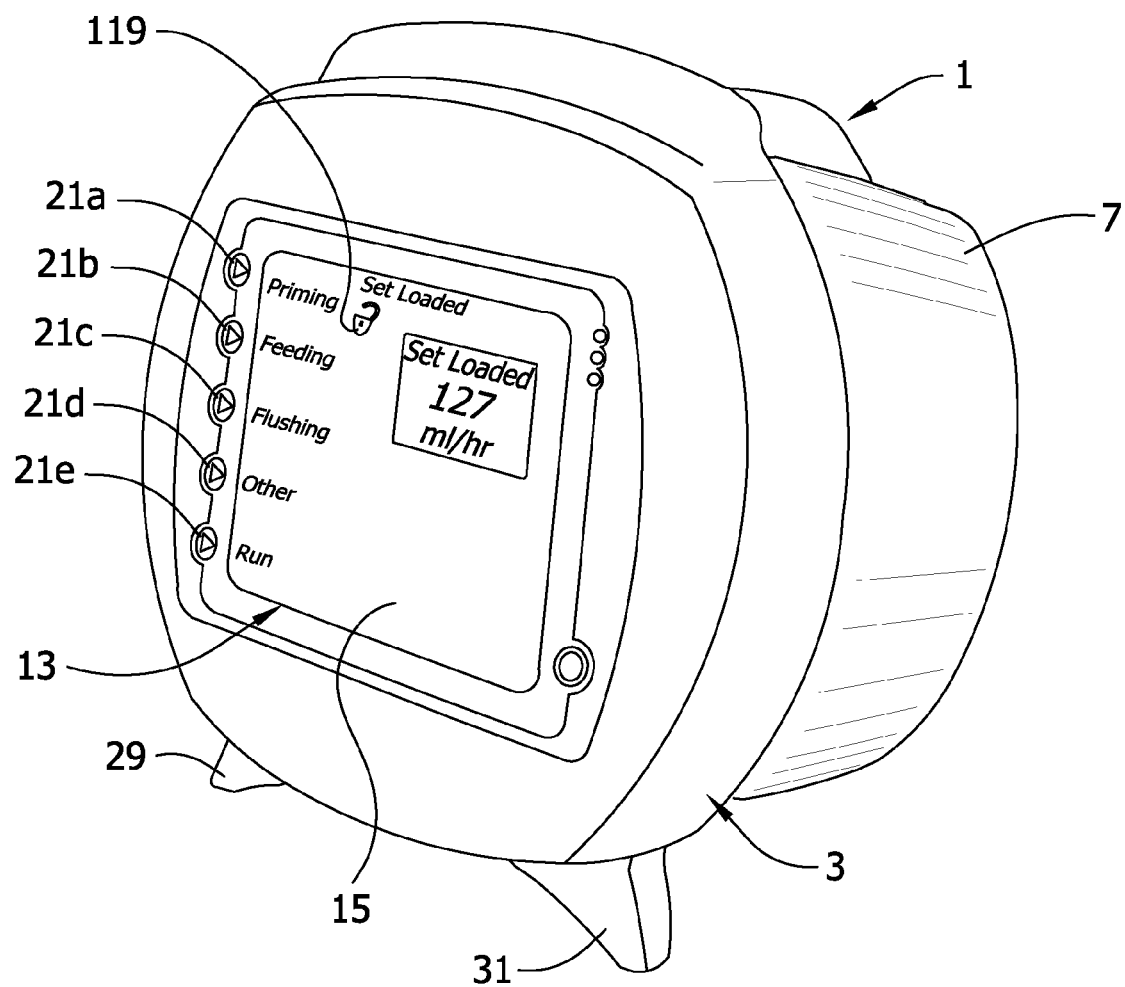
FIG. 1 is a perspective of an enteral feeding pump according to one exemplary embodiment of the invention.
Figure 2:
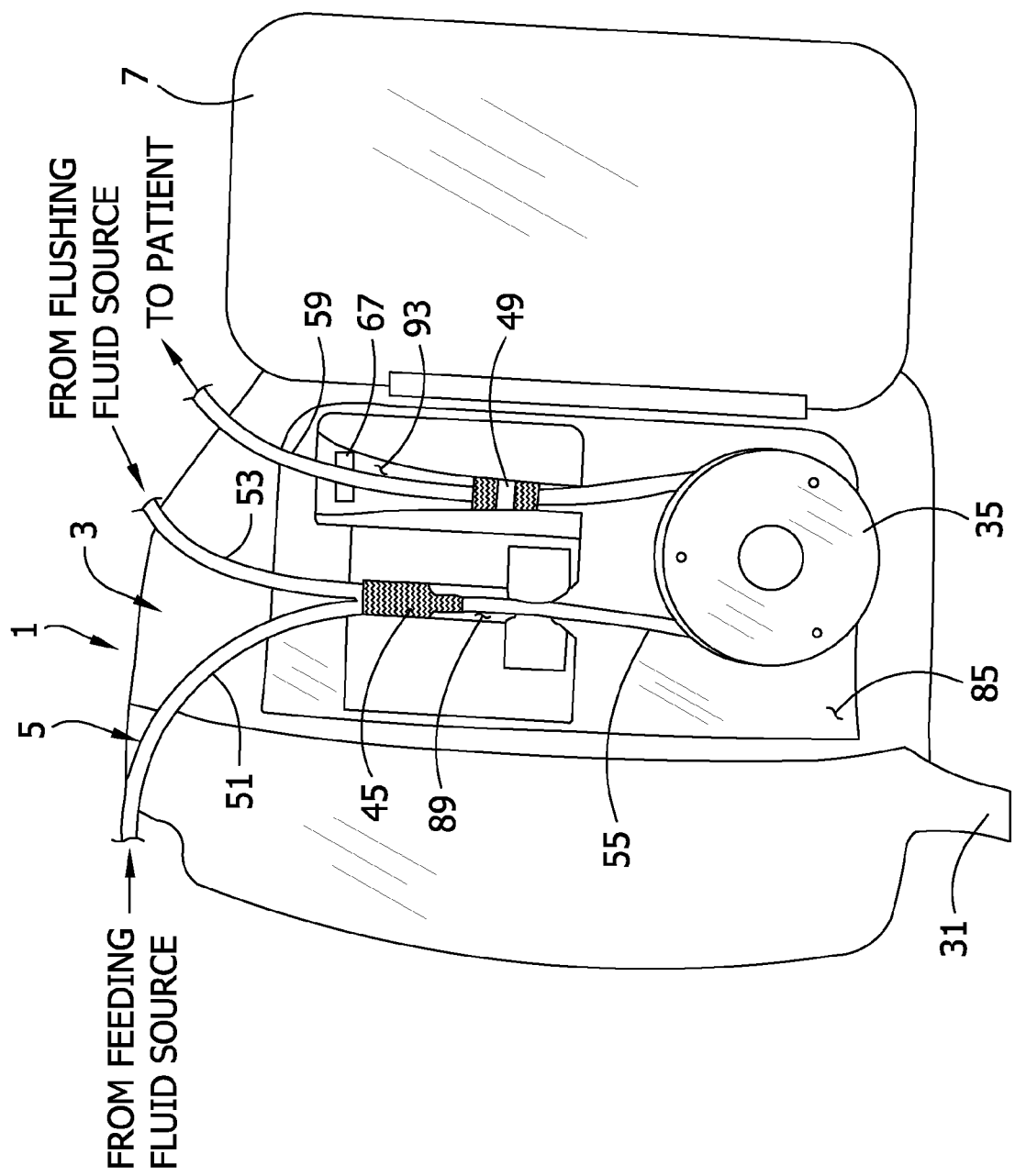
FIG. 2 is a side elevation thereof showing a fragmentary portion of an administration feeding set received in the pump according to one exemplary embodiment of the invention.

Referring now to the drawings, an enteral feeding pump (broadly, "pumping apparatus") constructed according to the principles of the present invention is generally indicated at 1. The feeding pump 1 comprises a housing, generally indicated at 3, that is constructed to receive an administration feeding set (broadly, "a pump set") generally indicated at 5. A fragmentary portion of the feeding set is shown in FIG. 2. Suitable pump sets are shown in co-assigned U.S. patent application Ser. No. 10/853,958 filed May 25, 2004 entitled FLOW CONTROL APPARATUS, the entire disclosure of which is incorporated herein by reference. The housing 3 includes a door 7 hinged to the remainder of the housing for swinging between a closed position (FIG. 1) and an open position (FIG. 2), which exposes a portion of the pump 1 that receives the administration feeding set 5. The pump 1 has a user interface, generally indicated at 13, including a display screen 15 on the front of the housing 3. The display screen 15 is capable of displaying information about the status and operation of the pump and a plurality of push buttons 21a, 21b, 21c, 21d, and 21e on the side of the display screen. The push buttons 21a thru 21e are provided for use in controlling and obtaining information from the pump 1. In the illustrated embodiment, the push buttons 21a thru 21e are used for selecting a respective operating mode of the pump such as the "PRIMING", "FEEDING", "FLUSHING", and "RUN" modes of the pump. Legs 29, 31 at the bottom front of the housing 3 support the housing 3 so that the display screen 15 is angled slightly upward for ease of viewing It will be understood that although the illustrated pump 1 is an enteral feeding pump, the present invention has application to other types of pumping apparatus, including medical infusion pumps. The pump 1 has a rotor 35 (FIG. 2) in the housing 3 that controls the flow of fluid through the feeding set 5. The general construction an operation of the enteral feeding pump 1, except as set forth hereinafter, may be generally the same as disclosed in co-assigned U.S. patent application Ser. Nos. 10/854,136 filed May 25, 2004 and entitled FLOW CONTROL APPARATUS, and U.S. Pat. No. 7,092,797 entitled FLOW MONITORING SYSTEM FOR A FLOW CONTROL APPARATUS, the entire disclosures of which are incorporated herein by reference. Moreover, although an administration feeding set 5 is shown, other types of pump sets (not shown) can be used within the scope of the present invention.

As shown in FIG. 2, the administration feeding set 5 includes a valve mechanism 45 and a mounting collar 49 that are loaded in the pump 1 for delivery of fluid to a patient. The feeding set includes a first section of tubing 51 upstream of the valve mechanism 45 leading to a feeding fluid source (not shown) and a second section of tubing 53 upstream of the valve mechanism leading to a flushing fluid source (not shown). The feeding set 5 includes a third section of tubing 55 downstream of the valve mechanism connecting the valve to the mounting collar 49 and a fourth section of tubing 59 leading from the mounting collar 49 to the patient. The valve mechanism 45 is operable to selectively permit flow of feeding fluid from the feeding fluid source (not shown) or a flushing fluid source, or prevent any fluid flow communication from the feeding or flushing fluid sources into the tubing 59 leading to the patient. When loaded into the pump 1, the valve mechanism 45 and the mounting collar 49 are securely engaged with the pump and the third section of tubing 55 is placed in a stretched condition between the valve mechanism 45 and the mounting collar 49 around the rotor 35 of the pump. The valve mechanism 45 may be similar to the valve mechanism is disclosed in co-assigned U.S. patent application Ser. No. 10/853,958 previously incorporated herein by reference. Various other operational features of the pump are disclosed in co-assigned U.S. patent application Ser. No. 10/854,008 filed May 25, 2004 and entitled RE-CERTIFICATION SYSTEM FOR A FLOW CONTROL APPARATUS, the entire disclosure of which is incorporated herein by reference.

The housing 3 of the pump 1 has an interior space 85 adapted for receiving the administration feeding set 5. The interior space 85 of the housing 3 is selectively enclosed by the door 7 mounted on the housing. The interior space 85 of the pump has a first chute 89 and a second chute 93 for receiving respective portions of the administration feeding set 5. The first chute 89 receives the valve mechanism 45 and the second chute 93 receives the mounting collar 49. The rotor 35 is located in the interior space 85 below the first and second chutes 89, 93 and engages the third section of the tubing 55 when the tubing section is placed in a stretched condition between the first and second chutes. Rotation of the rotor 35 compresses tubing 55 and provides a force for driving fluid in the feeding set 5 from the upstream side of the rotor to the downstream side of the rotor for delivery to the patient. A fluid detector 67 in the housing 3 is located in a position to detect the presence or absence of fluid in the section of tubing 59 downstream of the rotor 35.

Figure 3:
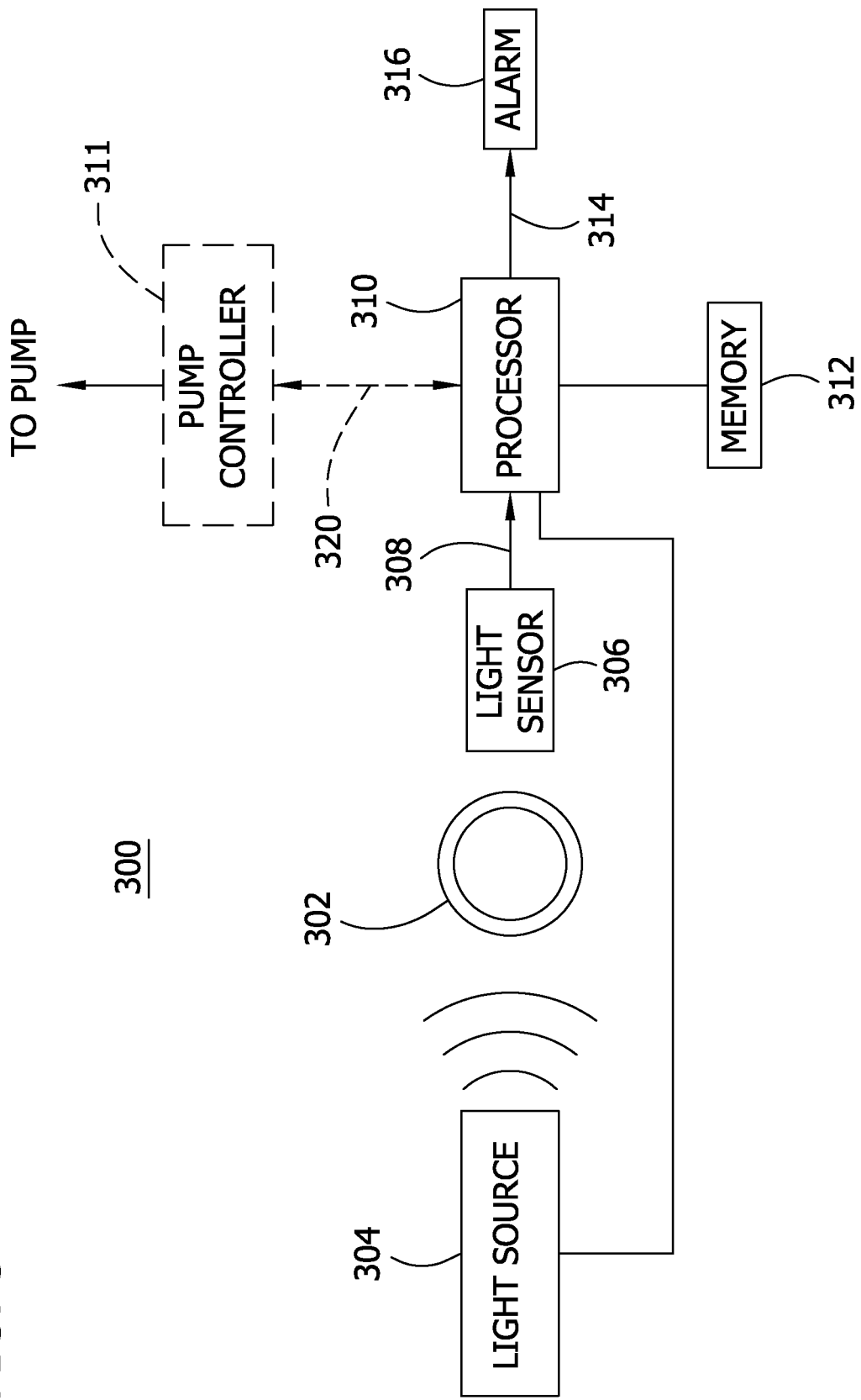
FIG. 3 is an exemplary block diagram illustrating components of a fluid detection system according to one exemplary embodiment of the invention.

Referring now to FIG. 3, an exemplary block diagram illustrates components of a system 300 (e.g., fluid detector 67) for detecting fluid in a section of tubing 302 (e.g., tubing 59) providing fluid to a patient. Notably, although the system 300 is described herein as being positioned to detect the presence or absence of fluid in a section of tubing 302 that is downstream from the rotor 35, it is contemplated that the principles and components described herein can be used to detect the presence or absence of fluid in a section of tubing (e.g., tubing 51) on the upstream side of the rotor 35.

A light source 304 positioned adjacent to a side of tubing 302 transmits light through the feeding tube and any fluid therein. In this particular embodiment, the light source 304 is an infrared light emitting diode (LED) that transmits infrared light through tubing 302. The light transmitted through tubing 302 is attenuated to some extent by the properties of tubing 302. If fluid is present in the tubing 302, the light being transmitted through tubing 302 is further attenuated. The extent to which the transmitted light is further attenuated by the presence of fluid depends on the opaqueness or translucency of the particular fluid present in the tubing 302. For example, if the fluid in the tubing 302 is more opaque (e.g., non-clear) such as a feeding formula, the light transmitted through the tubing 302 may be significantly attenuated. Alternatively, if the fluid in the tubing 302 is translucent (i.e., clear) such as water the light transmitted through the tubing 302 is more attenuated than when air is in the tubing 302, but is less attenuated than when a feeding formula is in the tubing 302.

A light sensor 306 positioned adjacent to an opposite side of the tubing 302 senses the intensity of the light transmitted through the tubing 302 and any fluid therein. For example, the light sensor 306 is a light to frequency (LTF) converter such as a TSL 235R LTF converter manufactured by TAOS Inc. of Plano, Tex., United States of America. The light sensor 306 is responsive to the intensity of transmitted light to generate an output signal, as indicated by 308, having a frequency that is a function of (e.g., proportional to) the sensed intensity of the transmitted light. As described above, the amount, or intensity, of light transmitted through the tubing 302 and, thus, sensed by the light sensor 306, depends on whether or not fluid is present in the feeding tube and the type of fluid present in the tubing 302. For example, when fluid is absent from the tubing 302 (i.e., air only) the frequency of the generated output signal 308 is approximately 130 kHz. As other examples, the frequency of the output signal 308 is approximately 25 kHz when a non-clear fluid such a feeding formula is in the tubing 302, and the frequency of the output signal 308 is approximately 185 kHz when a clear fluid such as water is in the tubing 302.

A microprocessor 310 is connected to the light sensor 306 to receive the generated output signal 308 and determine a parameter value of the output signal 308. The microprocessor can be any general purpose microprocessor such as, for example, a UPD78F4225 microprocessor manufactured by NEC Electronics Corporation of Kanagawa, Japan. According to one aspect of the invention the microprocessor 310 reads the output signal 308 and determines a frequency of the output signal, and, thus, can determine the absence, presence, and or type of fluid in the tubing 302. For example, a memory 312 linked to, or integrated with, the microprocessor 310 stores a data table such as shown below in the Table I. The microprocessor 310 can also be configured to provide a control signal (not shown) to the light source 304 to turn the light source 304 on or off.

TABLE I

| Content of Feeding Tube | Threshold Frequency Values (kHz) |
| --- | --- |
| Air | 125-135 |
| Clear Fluid | 180-190 |
| Non-Clear Fluid | 20-30 |

As can be seen, the data table includes a range of expected frequencies of the generated output signal 308 for various contents in the feeding tube. For example, frequencies between 125-135 kHz indicate no fluid (i.e., air) is in the tubing 302, frequencies between 180 and 190 kHz indicate a clear fluid such as water is in the tubing 302, and frequencies between 20-30 kHz indicate a non-clear fluid such as feeding formula is in the tubing 302.

Figure 4B:
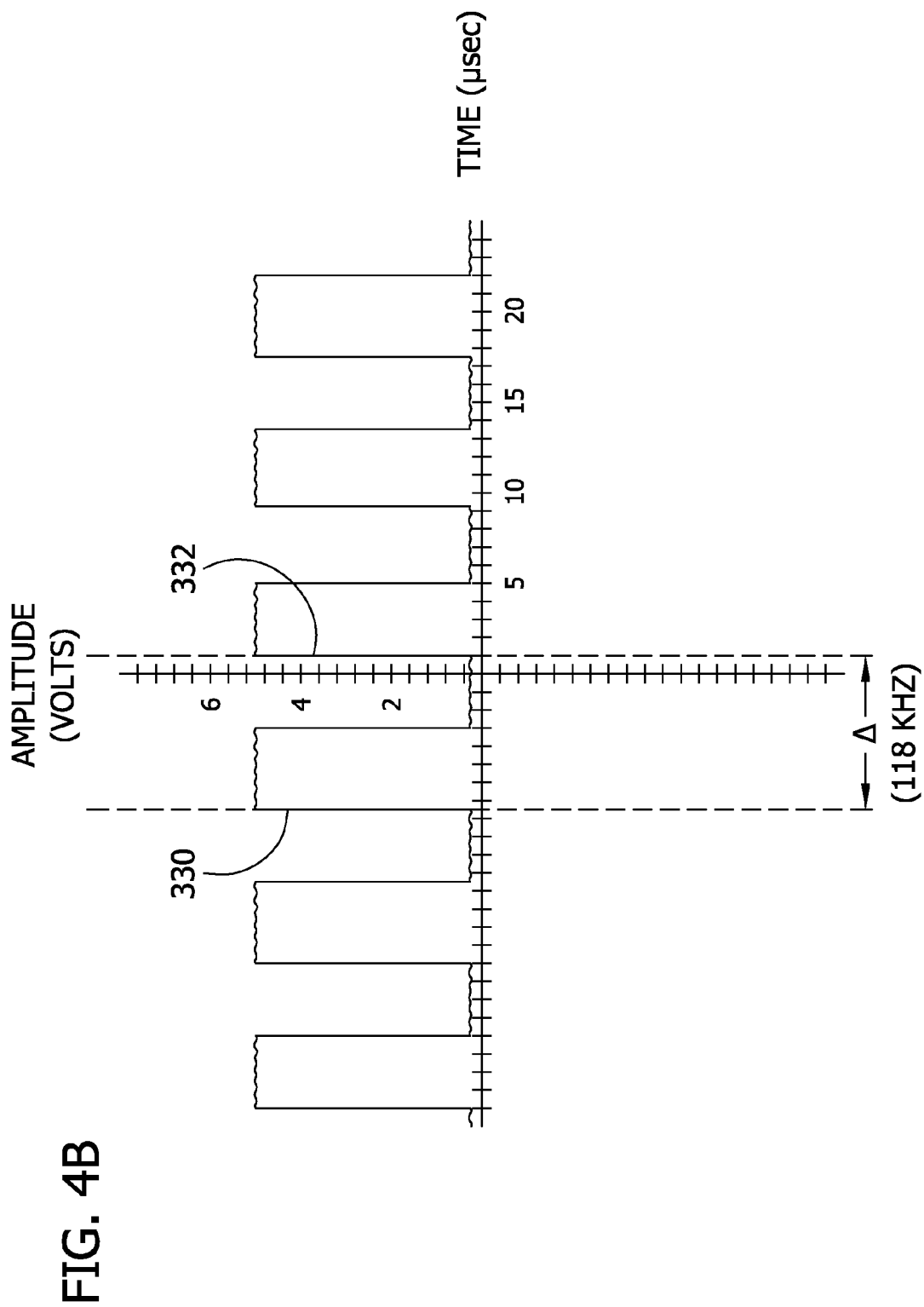

FIGS. 4A and 4B illustrate examples of measurements obtained by the system 300. In the example of FIG. 4A, tube 302 contains a feeding solution, such as Isocal® HN nutritional formula available from Novartis Medical Nutrition. The output signal generated by light sensor 306 has a frequency of about 25 kHz, as indicated by the Δ measurement of about 40 μseconds between a leading edge 326 and a leading edge 328. In the example of FIG. 4B, tube 302 is empty (i.e., it contains air). The output signal generated by light sensor 306 has a frequency of about 118 kHz, as indicated by the Δ measurement of about 8.45 μseconds between a leading edge 330 and a leading edge 332.

The microprocessor 310 generates an alarm signal, as indicated by 314, when the determined frequency of the output signal 308 indicates that no fluid (i.e., air) has been in the feeding tube for at least some minimum period of time. The minimum period of time depends on the expected flow rate of the fluid. For example, if the expected flow rate of the fluid is 5 milliliters per hour (ml/hr), the microprocessor 310 generates the alarm signal 314 when the frequency of the output signal 308 remains between 125-135 kHz for at least twenty-one (21) minutes. As another example, if the expected flow rate of the fluid is 300 ml/hr, the microprocessor 310 generates the alarm signal 314 when the frequency of the output signal 308 remains between 125-135 kHz for at least fifteen (15) seconds. An alarm 316 coupled to the microprocessor 310 is responsive to alarm signal 314 to provide a visual and/or audible indication to appropriate personnel there is an absence of fluid in the tubing 302.

According to another embodiment of the invention, the fluid detection system 300 determines whether fluid is flowing in the tubing 302. The microprocessor 310 is coupled to a motor drive circuit (not shown) such as included in a pump controller 311 of the pump 1 to receive the same motor drive pulse signal that drives the rotor 35 of the pump 1. As such, when the motor drive circuit activates the rotor 35 of the pump 1, the microprocessor 310 is responsive to the drive pulse signal to begin monitoring the generated output signal 308. More specifically, the microprocessor 310 determines whether the frequency of the generated output signal 308 changes over a predetermined period of time beginning from the time the motor drive pulse was received by the microprocessor 310. For example, when fluid is present in the tube 302 and there is no fluid flow, the frequency of the output signal 308 is approximately 25 kHz. However, when fluid starts moving in the tubing 302 due to rotor 35 rotation, the frequency of the output signal 308 increases between 30-60 Hz and lags the rotor rotation by approximately 0.5 seconds. In other words, some period of time passes (e.g., 5 seconds) after rotor rotation begins before the increase in the frequency of the output signal can be detected. After the rotor stops, the frequency of the output signal 308 decreases to the frequency level prior to rotation. This change or shift in frequency is detected by the microprocessor 310 and used in conjunction with the motor drive pulse to detect fluid flow. Notably, although the microprocessor 310 and pump controller 318 are illustrated as separate components it is contemplated that microprocessor 310 can be integrated into the pump controller.

According to another embodiment of the invention, the fluid detection system 300 operates as an occlusion detector. When there is an occlusion in the tubing 302, whether upstream or downstream of the light sensor 306, fluid cannot flow even if the rotor is rotating. As a result, the frequency of the generated output signal 308 will not change over the predetermined period. If the microprocessor 310 determines that the frequency of the generated output signal 308 does not changes over the predetermined period of time beginning from the time the motor drive pulse was received by the microprocessor 310, the processor 310 generates an alarm signal 314 to activate the alarm 316.

According to yet another embodiment of the invention, the fluid detection system 300 further operates as a bag empty detector to prevent the underfeeding of patients due to a lack of delivered formula. For example, when a bag (not shown) in fluid connection with the upstream side of the administration set for the purposes of supplying a feeding formula is empty, the fluid detection system 300 can be positioned to detect the absence of feeding formula in the upstream side of the tubing 55 of the feeding set 5. As described above, when there is no fluid in the tubing 55, the frequency of the generated output signal 308 is approximately 130 kHz. In this case, when a constant 130 kHz signal is detected by the microprocessor 310, an alarm signal is generated to indicate the presence of air in the tubing 55, which could be caused by an empty bag.

According to yet another embodiment of the invention, the fluid detection system 300 further operates in conjunction with a priming function of the pump to insure the feeding tube is fill or "primed" with a desired amount of fluid prior to connection to the tubing 302 supplying fluid to the patient. Priming in conventional feeding pumps is accomplished by, for example, an operator pressing an auto prime button (see priming button FIG. 2) on a control panel to begin a fixed number of rotations (e.g., 25) of the pump rotor 35 to begin filling the feeding tube with fluid. The number of fixed rotations is predetermined and is generally selected to insure that the feeding tube will contain a desired level of fluid. Unfortunately, due to liquid density, supply problems, or other reasons, it is possible that a particular fluid may not reach the desired level after the fixed number of rotations. As a result, the patient could receive less than a desired amount of medication or feeding formula.

By positioning the light source 304 and light sensor 306 at particular a point along the tubing 302 that corresponds to a location along the tubing 302 between the pump and an output end of the tubing 302 at which to fill with fluid, the guess work involved in determining an optimum number of fixed rotor revolutions to prime the feeding tube can be eliminated. In this configuration, the microprocessor 310 provides a primed signal, as indicated by 320, to the pump controller 311 when the processor 310 determines fluid is present at the desired level in the tubing 302. In operation, after the operator presses the priming button on the control panel, the pump rotor begins to rotate and continues to rotate until the pump controller receives the primed signal 320 from the microprocessor 310. Alternatively, in situations where it is not feasible to position the light source 304 and light sensor 306 exactly at the desired level, the pump controller can be configured to control the rotor to complete a few additional revolutions after receiving the primed signal 320 from the microprocessor 310 (e.g., 3-5) to insure the desired level reached.

Figure 5:
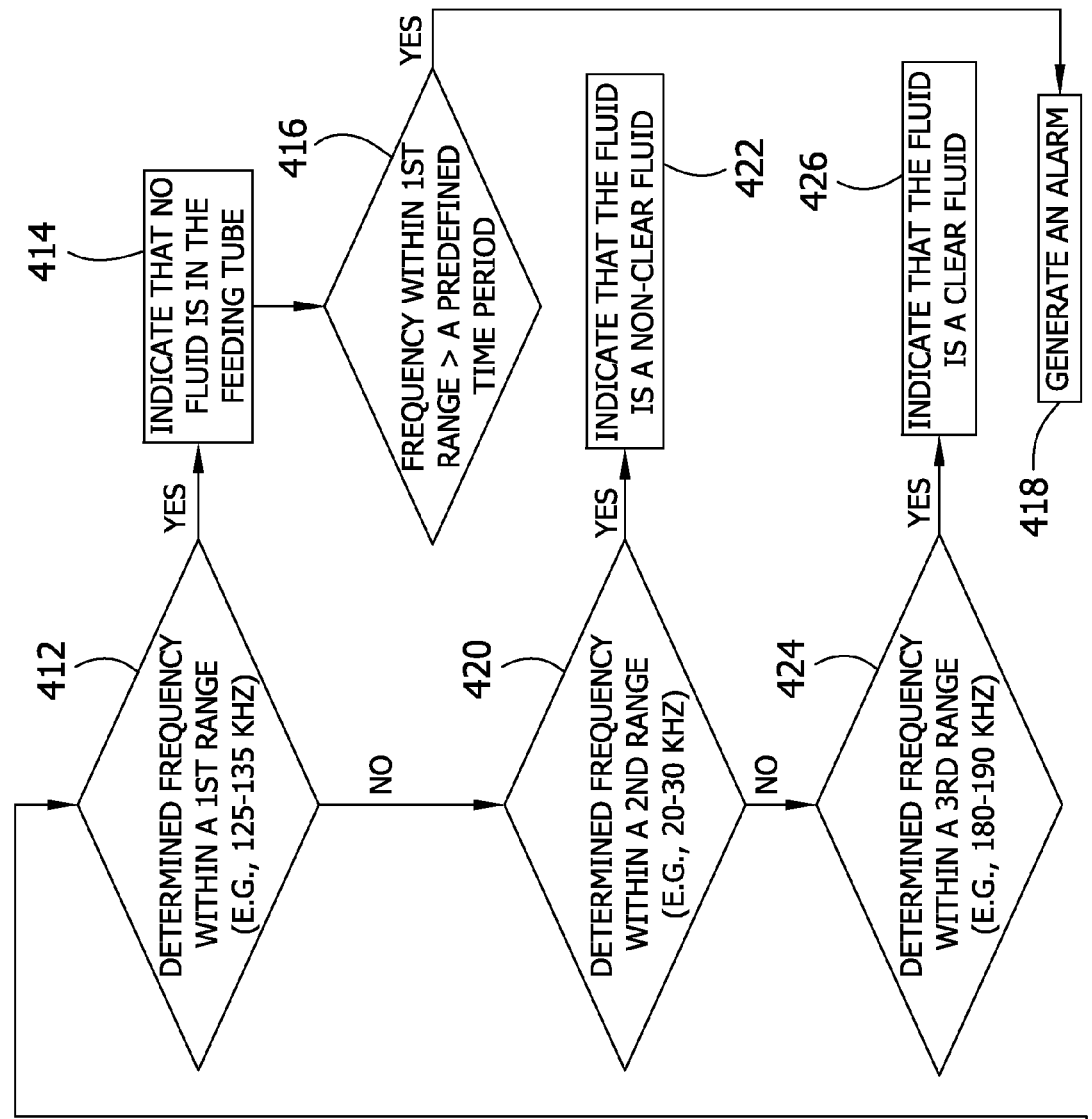
FIG. 5 is an exemplary flow chart illustrating a method for detecting the presence of fluid in a feeding tube according to one exemplary embodiment of the invention.
Figure 5:
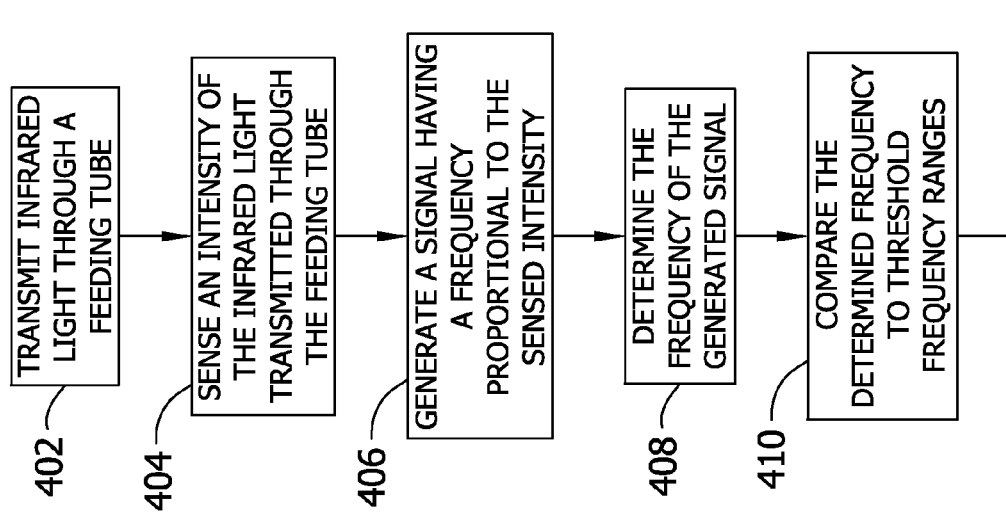

Referring now to FIG. 5, an exemplary flow chart illustrates a method for detecting the presence of fluid in a feeding tube according to one exemplary embodiment of the invention. For example, FIG. 5 illustrates software instructions for driving the microprocessor 310. At 402, an infrared light source is directed toward the feeding tube to transmit light thru the feeding tube. Light transmitted thru the feeding tube is sensed by a light sensor at 404. At 406, the light sensor is responsive to the intensity of the transmitted light to generate an output signal having a frequency as a function of the sensed intensity. In this instance, the output signal's frequency is proportional to the sensed intensity. A processor receives the generated output signal and determines the frequency of the generated output signal at 408. At 410, the processor compares the determined signal to a plurality of threshold frequency ranges to determine whether there is any fluid and/or the type of fluid in the feeding tube. If the frequency is determined to be within a first range such as between 125-135 kHz at 412, the processor determines that no fluid is in the feeding tube at 414. At 416, if the processor determines that the frequency remains within the first range for at least a predefined period of time such as 0.5 seconds, an alarm is generated to alert the appropriate personnel at 418. If the frequency is determined to be within a second range such as between 20-30 kHz at 420, the processor determines that a non-clear fluid such as feeding formula is in the feeding tube at 422. If the frequency is determined be in within a third range such as between 180-190 kHz at 424, the processor determines that a clear fluid such as water is in the feeding tube at 426.

Figure 6:
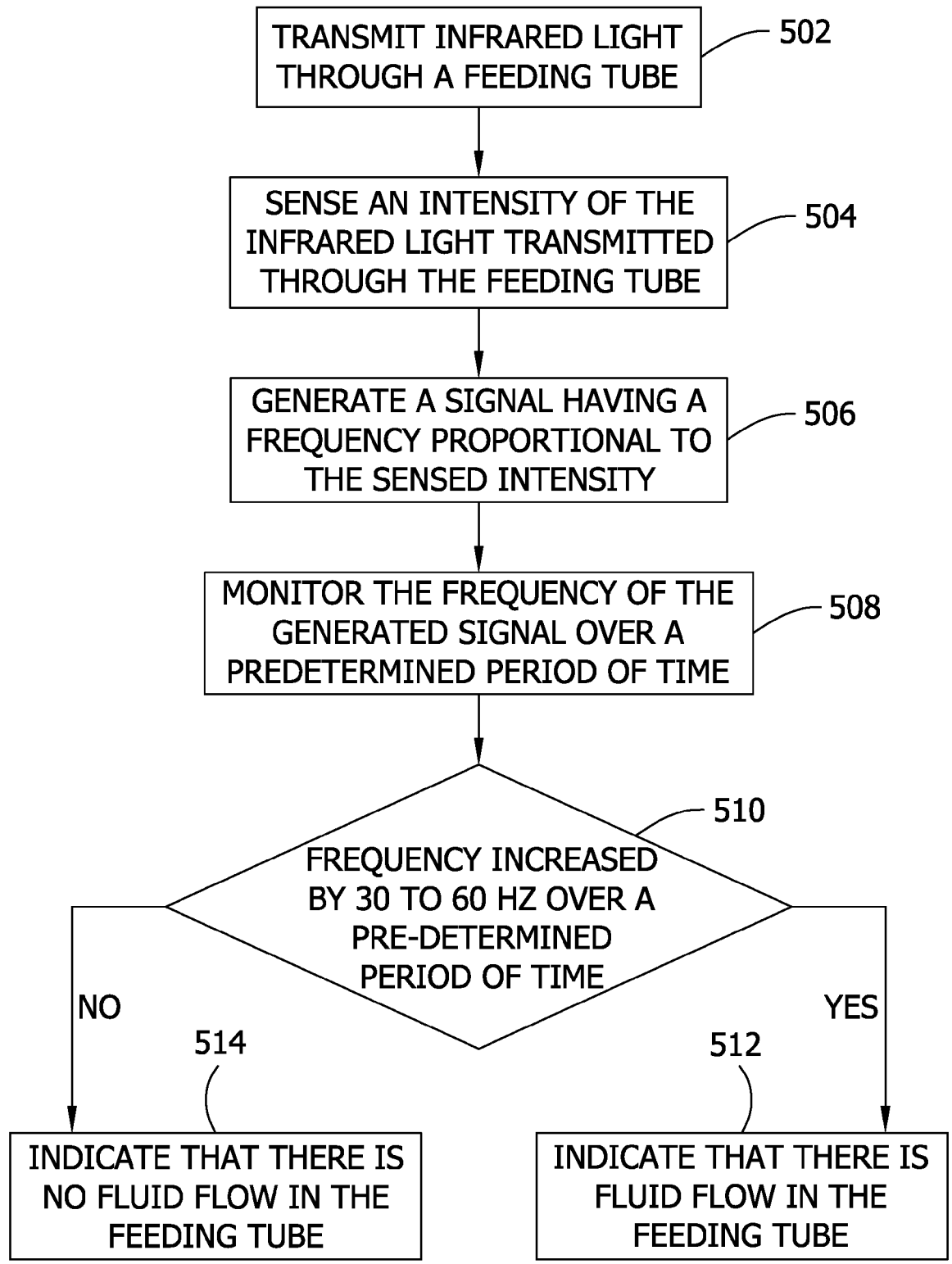
FIG. 6 is an exemplary flow chart illustrating a method for detecting fluid flow in a feeding tube according to one exemplary embodiment of the invention.

Referring now to FIG. 6, an exemplary flow chart illustrates a method for detecting fluid flow a feeding tube according to one exemplary embodiment of the invention. For example, FIG. 6 illustrates software instructions for driving the microprocessor 310. At 502, an infrared light source is directed toward the feeding tube to transmit light thru the feeding tube. The intensity of the light transmitted thru the feeding tube is sensed by a light sensor at 504. At 506, the light sensor is responsive to the sensed intensity of the transmitted light to generate an output signal having a frequency that is a function of (e.g., proportional to) the sensed intensity. A processor monitors the generated output signal to detect a change in the frequency of the output signal over a predetermined period of time at 508. If the frequency is determined to have increased between some minimum and maximum amount (e.g., 30-60 Hz) over the predetermined time period at 510, the processor determines that there is fluid flow in the feeding tube at 512. Alternatively, if it is determined that the frequency has not increased between the minimum and maximum amounts (e.g., 30-60 Hz) over the predetermined time period at 510, the processor determines that there is no fluid flowing in the feeding tube at 514.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A system for detecting fluid in a feeding tube, said system comprising:
   a light source transmitting an infrared light through the feeding tube and any fluid therein;
   an infrared intensity sensor sensing an intensity of the infrared light transmitted through the feeding tube and through any fluid therein and generating an output signal having a variable frequency, wherein the frequency of the output signal is a function of the sensed intensity of the infrared light transmitted through the feeding tube; and a processor receiving the generated output signal and determining the frequency of the generated output signal, wherein the processor is configured to determine whether fluid is in the feeding tube by comparing the determined frequency of the generated output signal to one or more threshold frequency ranges stored in a memory, and wherein said processor is configured to determine whether the feeding tube has no fluid, a clear fluid, or a non-clear fluid as a function of the determined frequency as compared to the threshold frequency ranges.

2. The system of claim 1, wherein the processor determines no fluid is in the feeding tube when the determined frequency is within a first threshold frequency range.

3. The system of claim 1, wherein the light source is an infrared light emitting diode, and wherein the threshold frequency ranges are 125-135kilohertz indicating no fluid, 180-195 kilohertz indicating a clear fluid, and 20-30 kilohertz indicating a non-clear fluid.

4. The system of claim 2 further including an alarm for alerting a user when the determined frequency is within the first threshold frequency range for at least a predetermined period of time.

5. The system of claim 1, wherein the processor determines a type of fluid in the feeding tube by comparing the determined frequency of the output signal to the stored one or more threshold frequency ranges.

6. The system of claim 5, wherein the feeding tube is a feeding tube supplying a fluid to a patient, and wherein the processor determines the type of fluid in the feeding tube is a clear fluid when the determined frequency is within a second threshold frequency range, and wherein the processor determines the type of fluid in the feeding tube is a feeding formula when the determined frequency is within a third threshold frequency range.

7. The system of claim 6 further comprising:
a pump having a motor for pumping fluid through the feeding tube;
a controller for controlling the motor to start or stop pumping of the fluid, said controller having an user interface for receiving input from a user to start pumping the fluid to fill the feeding tube with fluid to a particular point along the feeding tube;
wherein the light source and infrared sensor are positioned adjacent to the feeding tube at the particular point along the feeding tube;
wherein the processor provides a primed signal to a controller of the pump when the determined frequency is within the second or third threshold frequency ranges; and
wherein the controller is responsive to the primed signal to stop the pumping of the fluid in the feeding tube.

8. The system of claim 1, wherein the infrared sensor is a light-to-frequency converter.

9. The system of claim 1, wherein the processor further determines whether fluid is flowing in the feeding tube as a function of a change in frequency of the generated output signal over a predetermined period of time.

10. The system of claim 9, wherein the processor determines that fluid is flowing in the feeding tube when the frequency of the output signal changes by 30 to 60 hertz over the predetermined period of time.

11. A system for detecting fluid flow in a section of tubing of an administration set, said system comprising:
a pump having a motor for pumping the fluid through the tubing;
a light source positioned adjacent the tubing for transmitting an infrared light through the tubing and any fluid therein;
an infrared sensor positioned adjacent to the tubing for sensing an intensity of the transmitted infrared light and for generating an output signal having a variable frequency, wherein said frequency of the output signal is a function of the sensed intensity of the infrared light transmitted through the tubing; and
a processor receiving the generated output signal and determining a change in the frequency of the generated output signal over a predetermined period of time, and wherein said processor is configured to determine whether fluid is flowing in the tubing as a function of the determined change in frequency, wherein the processor determines whether the tubing has no fluid, a clear fluid, or a non-clear fluid by comparing the determined change in frequency of the output signal to a predefined frequency range stored in a memory.

12. The system of claim 11, wherein the processor determines that fluid is flowing in the tubing when the determined change in frequency of the output signal is between 30 and 60 hertz.

13. A method for detecting fluid in a feeding tube, said method comprising:
transmitting an infrared light through the feeding tube and any fluid therein;
sensing an intensity of the infrared light transmitted through the feeding tube and through any fluid therein;
generating an output signal having a variable frequency, wherein said frequency of the output signal is a function of the sensed intensity of the infrared light transmitted through the feeding tube;
determining the frequency of the generated output signal;
determining whether fluid is in the feeding tube by comparing the determined frequency of the generated output signal to one or more threshold frequency ranges stored in a memory; and
when fluid is determined to be in the feeding tube, determining whether the fluid in the feeding tube is a clear fluid or a non-clear fluid by comparing the determined frequency of the output signal to the stored one or more threshold frequency ranges.

14. The method of claim 13, wherein the threshold frequency ranges are 125-135 kilohertz indicating no fluid, 180-195 kilohertz indicating a clear fluid, and 20-30kilohertz indicating a non-clear fluid.

15. The method of claim 14 further including generating an alarm when the determined frequency is between 125 and 135 kilohertz for at least a minimum period of time.

16. The method of claim 13 further including determining whether fluid is flowing in the feeding tube as a function of a shift in the frequency of the generated output signal over a different predetermined period of time.

17. The method of claim 16, wherein fluid is determined to be flowing in the feeding tube when the frequency of the output signal shifts between 30 to 60 hertz over the different predetermined period of time.

18. A pumping apparatus for administering a fluid to a patient via a pump set loaded in the pumping apparatus, said pump set comprising tubing in fluid connection with a fluid source, said pumping apparatus comprising:
a pump for controlling fluid flow in the pump set, said pump being adapted for delivering fluid from the fluid source to the patient via the tubing of the pump set;

a light source for transmitting an infrared light through a portion of the tubing and any fluid therein when the pump set is loaded in the pumping apparatus;

an infrared intensity sensor responsive to the infrared light transmitted through the tubing and through any fluid therein for generating a variable frequency output signal, said frequency of the output signal being a function of an intensity of the sensed infrared light transmitted through the feeding tube and any fluid therein; and a processor, receiving and responsive to the output signal, is configured for comparing the frequency of the output signal to one or more threshold frequency ranges stored in a memory and for determining a fluid condition in the tubing as a function of the comparison, wherein the determined fluid condition is one of the following: no fluid, a clear fluid, and a non-clear fluid.

19. The pumping apparatus of claim 18, wherein the light source is an infrared light emitting diode (LED), and wherein the threshold frequency ranges comprise at least one of the following: 125-135 kilohertz indicating no fluid, 180-195 kilohertz indicating a clear fluid, and 20-30 kilohertz indicating a non-clear fluid.

20. The pumping apparatus of claim 18 further comprising an alarm for alerting a user when the determined fluid condition indicates an absence of fluid in the tubing for at least a predetermined period of time.

21. The pumping apparatus of claim 18, wherein the fluid condition comprises at least one of the following: an absence of fluid in the tubing, a presence of fluid in the tubing, and a type of fluid in the tubing.

22. The pumping apparatus of claim 21, wherein the type of fluid in the tubing comprises at least one of the following: an opaque fluid, a semi-opaque fluid, and a clear fluid.

23. The pumping apparatus of claim 21 further comprising:
a motor for driving the pump;
a controller for controlling the motor; said controller having a user interface for receiving input from a user to start pumping the fluid to fill the tubing with fluid to a predetermined position along the tubing;
wherein the light source and the infrared intensity sensor are positioned adjacent to the tubing at the predetermined position;
wherein the processor is configured for providing a prime signal to the controller in response to the frequency of the output signal indicating the presence of fluid in the tubing at the predetermined position; and
wherein the controller is responsive to the prime signal to stop the pumping of the fluid in the tubing and await further input from the user.

24. The pumping apparatus of claim 18, wherein the processor is configured to determine whether fluid is flowing in the tubing as a function of a change in the frequency of the output signal over a predetermined period of time.

25. The pumping apparatus of claim 24, wherein the change in the frequency of the output signal for determining whether fluid is flowing in the tubing comprises a frequency shift of about 30 to 60 hertz over the predetermined period of time.

* * * * *